United States Patent [19]

Fischer

[11] Patent Number: 5,269,684
[45] Date of Patent: Dec. 14, 1993

[54] ADJUSTABLE BRUSH DELIVERY TIP WITH SECONDARY FLOW PATH
[75] Inventor: Dan E. Fischer, Sandy, Utah
[73] Assignee: Ultradent Products, Inc., South Jordan, Utah
[21] Appl. No.: 940,204
[22] Filed: Aug. 31, 1992
[51] Int. Cl.⁵ .............................................. A61C 5/04
[52] U.S. Cl. .................................... 433/90; 604/310; 604/311
[58] Field of Search ............... 433/89, 90; 604/2, 3, 604/4, 184, 222, 310, 311; 132/75, 74.5, 73; 401/129

[56] References Cited

U.S. PATENT DOCUMENTS

| | | | |
|---|---|---|---|
| 374,026 | 11/1887 | Williams . | |
| 392,006 | 10/1888 | Carmichael . | |
| 762,603 | 6/1904 | Witkowski . | |
| 833,044 | 10/1906 | Goodhugh . | |
| 860,555 | 7/1907 | Middaugh . | |
| 870,573 | 11/1907 | Myers . | |
| 977,825 | 1/1910 | Murphy . | |
| 1,115,561 | 11/1914 | Northey . | |
| 1,164,430 | 12/1915 | Thurman . | |
| 1,245,153 | 11/1917 | Evslin . | |
| 1,438,064 | 12/1922 | Simmons . | |
| 1,573,224 | 2/1926 | Condit . | |
| 1,711,352 | 4/1929 | Jeffreys . | |
| 1,711,516 | 5/1929 | Alland . | |
| 1,908,403 | 5/1933 | Budde . | |
| 2,090,354 | 8/1937 | Massman . | |
| 2,100,157 | 11/1937 | Chandler | 128/269 |
| 2,104,651 | 1/1938 | Hoffman | 132/73 |
| 2,170,222 | 8/1939 | Strauss | 128/269 |
| 2,643,655 | 6/1953 | McKay | 128/220 |
| 2,754,590 | 7/1956 | Cohen . | |
| 2,902,035 | 9/1959 | Hartley | 128/234 |
| 3,175,242 | 3/1965 | Kamondy | 15/559 |
| 3,234,918 | 2/1966 | Gigli | 120/45.4 |
| 3,270,743 | 9/1966 | Gingras | 128/215 |
| 3,337,095 | 8/1967 | Marbach et al. | 222/309 |
| 3,346,147 | 10/1967 | Higgins et al. | 222/326 |
| 3,369,543 | 2/1968 | Ronco | 128/269 |
| 3,434,209 | 3/1969 | Weissman | 33/15 |
| 3,462,840 | 8/1969 | Ellman | 32/60 |
| 3,512,526 | 5/1970 | Fielding | 128/239 |
| 3,519,364 | 7/1970 | Truhan | 401/177 |
| 3,572,337 | 3/1971 | Schunk | 128/222 |
| 3,581,399 | 6/1971 | Dragan | 32/60 |
| 3,587,575 | 6/1971 | Lichtenstein | 128/215 |
| 3,759,259 | 9/1973 | Truhan | 128/269 |
| 3,760,503 | 9/1973 | Baskas | 128/218 |
| 3,792,699 | 2/1974 | Tobin et al. | 128/2 W |
| 3,894,538 | 7/1975 | Richter | 128/260 |
| 3,896,552 | 7/1975 | Russell | 32/34 |
| 3,910,706 | 10/1975 | Del Bon | 401/134 |
| 3,918,435 | 11/1975 | Beall et al. | 128/2 W |
| 3,924,623 | 12/1975 | Avery | 128/269 |
| 3,938,898 | 2/1976 | Reitknecht | 401/183 |
| 4,030,496 | 6/1977 | Stait et al. | 128/215 |
| 4,143,428 | 3/1979 | Cohen | 3/36 |
| 4,157,709 | 6/1979 | Schuster et al. | 128/759 |
| 4,225,254 | 9/1980 | Holberg et al. | 401/119 |
| 4,243,035 | 1/1981 | Barrett | 128/215 |
| 4,318,403 | 3/1982 | Sneider | 128/232 |
| 4,329,990 | 5/1982 | Sneider | 128/239 |
| 4,522,593 | 6/1985 | Fischer | 433/136 |
| 4,551,100 | 11/1985 | Fischer | 433/218 |
| 4,578,055 | 3/1986 | Fischer | 433/2 |
| 4,813,871 | 3/1989 | Friedman | 433/90 |
| 4,941,873 | 7/1990 | Fischer | 604/54 |
| 4,997,371 | 3/1991 | Fischer | 433/90 |

Primary Examiner—Gene Mancene
Assistant Examiner—Nicholas D. Lucchesi
Attorney, Agent, or Firm—Workman Nydegger Jensen

[57] ABSTRACT

An apparatus for applying coatings to various surface types. The apparatus includes a dispenser for holding a quantity of the coating material and a delivery tip having adjustable bristles at one end. The bristles are slidably secured in a spiral passageway formed by a helical ridge inside the delivery tip, thereby allowing the coating material to be continuously applied without the need to stop the procedure and rewet the applicator. The applicator permits accurate control of the amount of coating material applied to the surface. In this way, the surface receives neither an excessive nor an insufficient amount of the coating material. Moreover, the bristles may be pushed in to permit the coating material to be applied to a small, irregular surface, such as pits and fissures, or pulled out to permit the bristles to fan out for application to broad surface areas. Delivery of relatively viscous coating materials is made easier by providing the spiral passageway around the bristles so that the coating material does not have to flow through the bristles.

34 Claims, 3 Drawing Sheets

ADJUSTABLE BRUSH DELIVERY TIP WITH SECONDARY FLOW PATH

BACKGROUND

1. The Field of the Invention

The present invention relates to apparatus for delivering relatively viscous materials to various surface types. More particularly, the present invention is ideally suited for applying dental agents, such as impression material, sealing, etching, bonding, restoring and/or other treatment agents, all hereinafter collectively referred to as dental agents, to teeth surfaces. This invention is also potentially useful in many other applications in addition to the field of dentistry, such as cosmetics, for example, applying fingernail polish, or electronic or mechanical assemblies requiring application of adhesives or coatings, to name just a few.

2. The Prior Art

Bonding agents play an important role in dental restorative techniques. Generally, bonding agents are applied to tooth surfaces in order to firmly attach a restoration to the tooth. When the restoration is a composite resin restoration, the composition of the bonding agent is usually that of the matrix of the composite resin.

Before applying a bonding agent, the enamel around a cavity preparation is etched with acid. Acid etching of enamel creates micro-irregularities on the enamel surface. The resin in the bonding agent is usually diluted with monomers so that it has a low viscosity which can readily penetrate into the microscopic irregularities and undercuts produced by the acid etching. The bonding agent is then polymerized. It is believed that when the composite restorative resin is inserted into the cavity, it will polymerize to the bonding agent present on the cavity surface. In this way, better adaptation to the enamel walls of the cavity is achieved with improved mechanical retention of the restoration.

Various devices have been used in the art for applying dental bonding agents to tooth surfaces. One device used to apply dental bonding agents is a small porous sponge or swabbing material. In practice, a quantity of bonding agent is applied to a transfer pad. A sponge is then grasped with forceps and dipped into the bonding agent. The wetted sponge is then rubbed across the tooth surface in order to apply the bonding agent.

The small sponges are disposable to prevent cross contamination. However, the sponges do not permit accurate application of the bonding agent. Frequently, the bonding agent is applied to surrounding surfaces which do not need treatment. Moreover, the rubbing action required to apply the bonding agent necessarily damages the fragile crystalline surface structure of the tooth formed during acid etching. Once the crystalline surface structure of the tooth is damaged, its bondability is reduced.

Another existing device for applying bonding agent to tooth surfaces is a small disposable brush tip. Like the sponge, the brush tip must be held with forceps or some other holding device. The brush tip is then dipped into a quantity of bonding agent placed on a transfer pad.

Like the sponge, the brush tip is disposable. In addition, the brush tip does not damage the fragile crystalline structure of the tooth surface produced by acid etching. However, like the sponge, the brush tip must constantly be rewetted by the bonding agent during the dental procedure. This action tends to incorporate tiny microbubbles. Moreover, the disposable brush tips used in the art usually have long bristles which do not form a fine tip. As a result, the bonding agent is often inadvertently applied to surrounding tooth surfaces.

Yet another device for applying bonding agents to tooth surfaces is a very fine paint brush. Such a brush can apply the bonding agent to tooth surfaces with precision and detail.

Despite its advantages, a paint brush must also be repeatedly dipped into a quantity of bonding agent during the procedure. In addition, a paint brush is difficult to properly sterilize and is usually nondisposable, thereby making it difficult for the dentist to maintain an aseptic environment. With the ever-increasing threat of Acquired Immune Deficiency Syndrome ("AIDS") in society, use of a nondisposable applicator which is also difficult to sterilize has become unacceptable.

Further, in each of the known devices for applying bonding agents to tooth surfaces, a quantity of bonding agent is placed on a transfer pad so that the device can be rewetted during the surgical procedure. Such a technique is not only wasteful, but it exposes the bonding agent to light, air, and airborne contaminants, light being significantly detrimental as most resin-based systems used by dentists are light activated.

Moreover, time is often of the essence in applying bonding agents to tooth surfaces, both to the dentist and due to working conditions such as when working on young children that may squirm, or in order to avoid contamination. As a result, it is important for bonding agents to be applied quickly and accurately. Thus, the need to constantly rewet the bonding agent applicator during the procedure is not only inefficient, but may reduce the effectiveness of the resulting bond between the restoration and the tooth surface. Many of these same problems exist when applying other types of dental agents.

In an attempt to solve many of these problems, an apparatus has been devised that includes a syringe-type dispenser for holding the quantity of dental agent and a removable applicator tip having bristles at one end. The bristles are in communication with the syringe-type dispenser, thereby allowing the dental agent to be continuously applied to the tooth surfaces without the need to stop the dental procedure and re-wet the applicator. This device is more particularly disclosed in my prior U.S. Pat. No. 4,997,371, incorporated herein by reference.

While this device is very effective and solves many of the problems discussed above, it has been found that there are still some problems that exist with that device. For example, the bristles which are held by the applicator tip are primarily held by the frictional grip which occurs at the distal end of the tip. This causes the bristles to act as a filter, particularly with respect to any filler particles that are contained in the dental agent. Such filtering may change the physical properties of the particular agent, such as a bonding agent and may make the actual bond weaker. Sometimes such filtering can even tend to choke off the delivery tip, preventing flow of material. In such cases, if a dentist does not use appropriate restraint, attempting to force the flow of material through a clogged tip may actually cause the tip to be blown off, expelling undesired quantities of the material into the patient's mouth.

Furthermore, in this type of device, the fiber count is critical because if there are not enough fibers, even to the extent that there are only two or three fibers too few, the bristles will tend to push back into the tip and will not be held by the frictional grip at the distal end. On the other hand, if too many fibers are included, so that even two or three fibers too many are found in the brush, the plastic material at the end of the tip will tend to split. This, of course, substantially complicates the manufacturing process, making it much more time consuming and tedious in order to assure very close tolerance on the fiber count in order to avoid the mentioned problems. Moreover, even if the fiber count is exact, the problem of filtering filler particles tends to remain.

BRIEF SUMMARY AND OBJECTS OF THE INVENTION

The present invention seeks to resolve the above and other problems which have been experienced in the art. More particularly, the apparatus of this invention constitutes an important advancement in the art of dental agent or other coating applicators, as evidenced by the following objects and advantages realized by the invention over the prior art.

One object of the present invention is to provide apparatus and methods of coating various surface types which permit continuous, bubble-free application without the need to stop and rewet the applicator by dipping it.

Another important object of the present invention is to provide apparatus and methods of applying coatings to various surface types which permit either pin-point or broad-brush type application of the coating to the area that needs treatment.

An additional important object of the present invention is to provide an apparatus for applying coatings to various surface types which is conducive to being disposable.

Still another object of the present invention is to provide apparatus and methods of applying coatings to various surface types which permit the coating to be applied directly from a source not exposed to air, light, and airborne contaminants.

A further important object of the present invention is to provide apparatus and methods of applying coatings to various surface types which does not require the use of a transfer pad or well.

Yet another important object of the present invention is to provide apparatus and methods of applying coatings to various surface types which give greater control over the flow of the coating to the surface.

Still another important object of the present invention is to provide an apparatus and method for delivery of coatings to various surface types which permit a plurality of bristles that are used to form a brush to be slidably secured within a delivery tip in such a way that the bristles do not filter out filler particles within the coating that is to be applied, and which also eliminates to a significant extent the need for maintaining a critical count as to the number of bristles used to form the brush.

Additional objects and advantages of the invention will be apparent from the description which follows, or may be learned by the practice of the invention.

The apparatus of the present invention includes a dispenser such as a syringe, squeeze bulb or the like for holding a quantity of dental agent or other coatings and a delivery tip having bristles at one end. The delivery tip may be curved or straight to accommodate access to the desired surface undergoing treatment. The bristles are slidably secured by one or more ridges that are preferably but not necessarily helical ridges. The spaces between the ridge or ridges form one or more channels around the bristles, and in the case of a helical ridge, the spaces between the ridge form a tapered, spiral passageway or channel (hereinafter collectively referred to as passageway) around the bristles. The spiral or other passageway enhances delivery of the dental agent or coating by permitting flow around the bristles and out the distal end of the tip, so that the bristles do not filter any filler particles that may be present.

The dental agent or coating remains in the dispenser until applied directly to the surface. In this way, the dental agent or coating is not exposed to light, air, and airborne contaminants. In addition, there is no need for a transfer pad and rewetting.

The applicator of this invention permits accurate control over the amount of dental agent or coating applied to the surface. Thus, the surface receives neither an excessive nor an insufficient amount of the dental agent or coating. Moreover, the bristles permit the dental agent or coating to be applied to the surface without damaging fragile structure.

BRIEF DESCRIPTION OF THE DRAWINGS

In order to more fully understand the manner in which the above-recited advantages and objects of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the presently preferred embodiments and the presently understood best mode of the invention as applied in the context of a dental agent applicator will be described with additional detail through use of the accompanying drawings in which.

DETAILED DESCRIPTION OF THE PRESENTLY PREFERRED EMBODIMENT

Figures 4, 5:
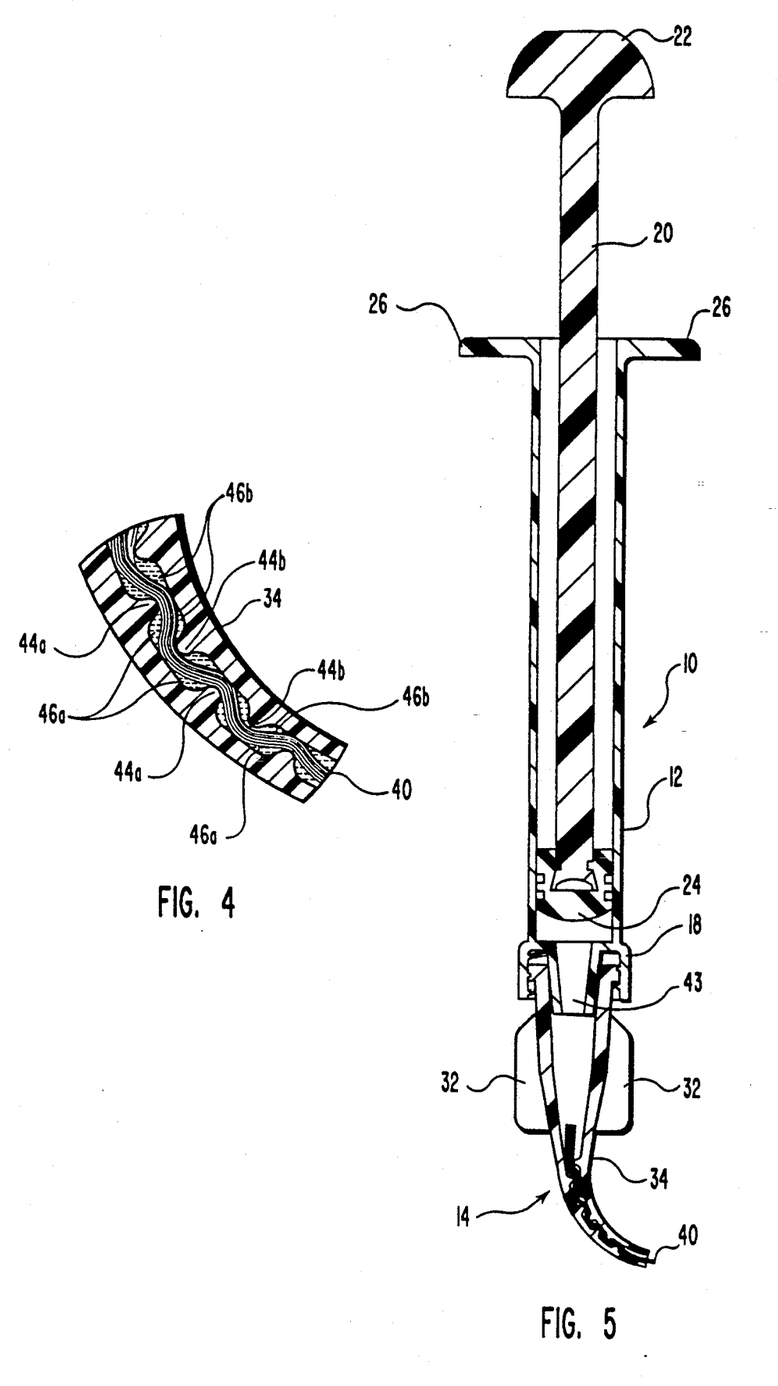
FIG. 4 is an enlarged cross-sectional view of the end of the syringe delivery tip taken along lines 4—4 of FIG. 2, so as to more particularly illustrate the manner in which the bristles are slidably secured by a helical ridge which forms a spiral passageway through the interior of the syringe delivery tip.
FIG. 5 is a longitudinal sectional view of the entire apparatus, including the syringe delivery tip as connected by a luer-lock coupling to a syringe apparatus which is used for controlling the delivery of a dental agent or coating through the delivery tip.

Reference is now made to the drawings wherein like parts are designated with like numerals throughout. Referring first to FIG. 5, one presently preferred embodiment of the apparatus of the present invention is illustrated and generally designated 10.

Applicator 10 includes a syringe barrel 12 and delivery tip 14 Syringe barrel 12 is generally cylindrical in shape and is adapted for holding a quantity of dental agent or other coating.

In the embodiment of the present invention illustrated in FIG. 5, delivery tip 14 is removable. Affixed to the lower end of syringe barrel 12 is a female luer-lock coupling 18. Removable delivery tip 14 is secured to syringe barrel 12 through coupling 18. Other means may be used to couple the delivery tip 14 to the syringe barrel 12. For example, a screw fit or press-fit coupling mechanism is suitable.

In another embodiment within the scope of the present invention, delivery tip 14 is permanently secured to the syringe barrel 12. The delivery tip 14 may be integrally molded as part of the syringe barrel 12 or it may snap on irreversibly to the syringe barrel 12. In such an embodiment, the syringe barrel 12 could be configured to hold only a sufficient quantity of dental agent or other coating for a single application. Thereafter, the device could be discarded.

Longitudinally slidable within syringe barrel 12 is plunger 20. Plunger 20 has at its proximal end a thumb disk 22 and at its distal end a plunger head 24. Plunger head 24 is constructed out of a resilient material such that its outer edge is contiguous with the inner wall of the syringe barrel 12. In addition, plunger head 24 is preferably constructed of a material which is non-reactive with the dental agent or coating.

At the proximal end of syringe barrel 12 is a pair of finger wings 26. Although conventional syringes function by placing two fingers on the finger wings 26 and depressing thumb disk 22 with the thumb, the present invention is preferably used by placing the fingers and thumb around syringe barrel 12 and depressing thumb disk 22 by the palm of the hand. This unique method of use gives the dentist or other user greater control in applying the dental agent or coating. Plunger 20 longitudinally enters syringe barrel 12. As a result, plunger head 24 presses against the dental agent or coating causing it to flow out of syringe barrel 12 and through the delivery tip 14.

Figure 1:
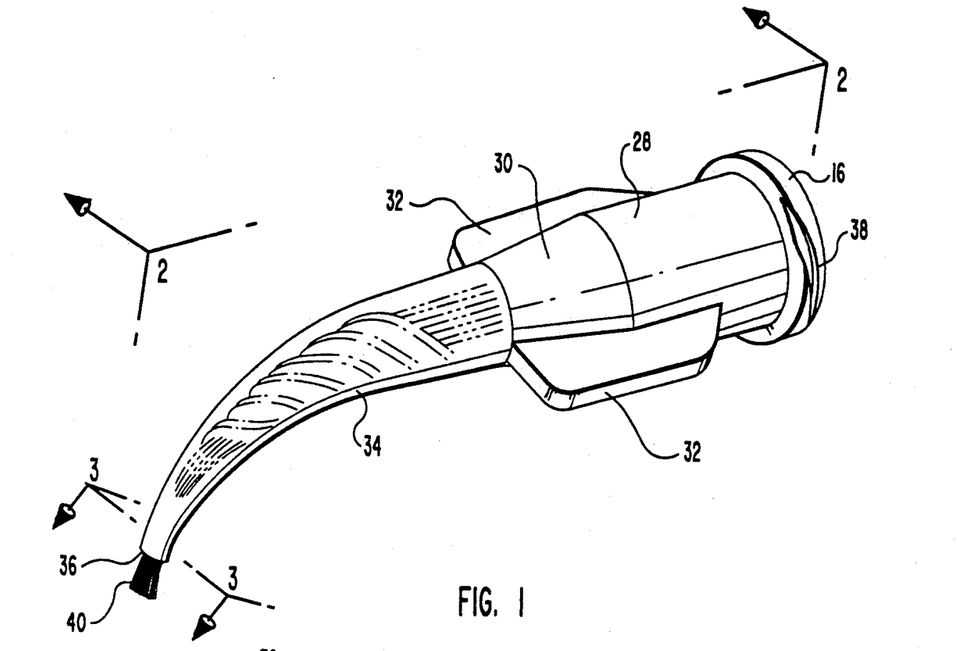
FIG. 1 is a perspective view of the presently preferred embodiment of the syringe delivery tip of the present invention.

The delivery tip 14 is more particularly illustrated with references to FIGS. 14, taken together. As shown best in FIG. 1, at the proximal end of the delivery tip 14, there is a male luer-lock threaded coupling 16 which is designed to mate with the corresponding female luer-lock coupling 18 of the syringe barrel 12. The delivery tip 28 has a cylindrical hub 28 which is tapered through conical section 30 and which joins to a nozzle 34, which may be curved as shown, or straight. Held within the curved nozzle 34 is a plurality of bristles 40, which as more particularly described hereinafter, can be used for application of the dental agent or coating using either a pin-point type application or a fanned out broad-brush type application Also formed near the proximal end of the delivery tip 14 is a pair of fins 32 which are provided for convenience in threading the delivery tip 14 onto the syringe barrel 12.

Figure 2:
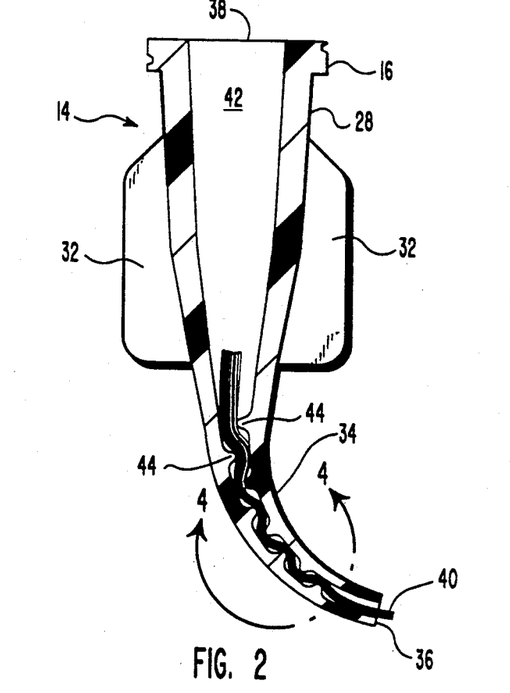
FIG. 2 is a longitudinal cross-sectional view of the embodiment of FIG. 1 taken along lines 2—2.

As shown best in FIG. 2, the interior of the delivery tip 14 forms a passageway 42 which at its proximal end 38 is in communication with an outlet nozzle 43 (See FIG. 5) from which the dental agent or coating is discharged from the interior of the syringe barrel 12 into the passageway 42 of the delivery tip 14. Passageway 42 could take any desired cross-sectional shape, such as circular, elliptical, or even square, rectangular or polygonal. The passageway 42 is tapered from the proximal end 38 of the passageway 42 to the distal end 36.

Furthermore, as shown best in FIGS. 2 and 4 taken together, a helical ridge 44 is formed through a portion of the passageway 42. The spaces 46b between the ridge 44 form a spiral passageway in which the bristles 40 are slidably secured. Because the ridge 44 is formed as a helix through the interior of the passageway 42, as shown best in FIG. 4, on one side of the passageway 42 the helical ridges 44a project into the middle of the channels or spaces 46b formed between the ridges 44b on the other side of the passageway 42. Similarly, the helical ridges 44b on the other side of passageway 42 project into the middle of the spaces 44a in an alternating fashion. This causes the bristles 40 to be secured by the helical ridge 44 in a helical, undulating fashion as shown in FIGS. 2 and 4.

It has been found that by correctly dimensioning the ridge 44 in relation to the size and number of bristles 40 used in the brush, the brush slides when pushed or pulled, due to the friction by which the undulating bristles 40 are held by ridge 44. In a preferred embodiment, the ridge 44 is, for example, of from 0.004 to 0.005 inches high for the size bristles described below.

Importantly, the space 46 (see FIG. 4) which is left around the outside of the bristles 40 forms a tapered, spiral or helical passageway which enhances the delivery of the dental agent or coating when it is dispensed by means of pressing the plunger 20 into the syringe barrel 12. The spiral passageway 46 actually enhances the flow of the dental agent or coating around rather than through the bristles 40 and makes the delivery of the dental agent or coating much easier than if it were forced to flow through the bristles 40.

Although the preferred embodiment has been illustrated using a single helical ridge 44, it is to be understood that any means of providing flow of the dental agent or coating around but not through the bristles is in keeping with the spirit and scope of the teaching of the present invention. For example, the spiral passageway could also be formed by forming two or more helical ridges opposing one another, such as two ridges 180° out of phase with one another. The passageway 46, though shown as a helical, spiraling passageway, could also take other forms. For example, a plurality of straight ridges might be used or the delivery tip could even have grooves formed in the interior wall of passageway 42 so as to form straight or spiral pathways through which the dental agent or coating could flow around, but not through, the bristles so as to enhance the ease of delivery.

Figure 3:
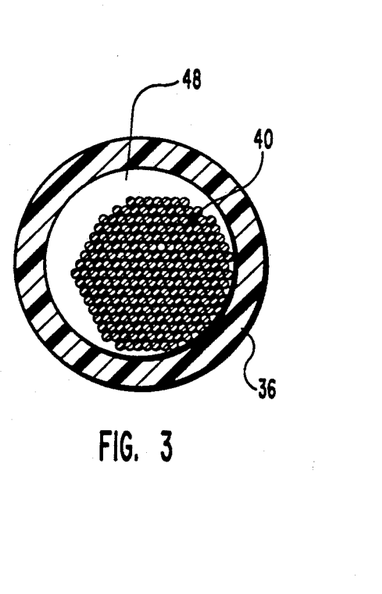
FIG. 3 is a cross-sectional view taken along lines 3—3 of the embodiment of FIG. 1 so as to particularly illustrate the manner in which the bristles do not occlude the distal end of the syringe delivery tip.

As will be further appreciated particularly in reference to FIGS. 2 and 3, the ridge 44 preferably terminates prior to the distal end 36 of the delivery tip 14. The bristles 40 also do not need to be frictionally held by the distal end 36 of the delivery tip 14 as in the case of the prior art type device described above since they are held by ridge 44. Thus, there is a space 48 (See FIG. 3) at the distal end 36 of the delivery tip 14 through which the dental agent or coating is permitted to flow as it exits the delivery tip 14 and which also permits the dental agent or coating to be better dispersed among the bristles 40.

Because the bristles 40 are slidably secured by the helical ridge 44 which is located at the interior of the passageway 42, the bristle count does not need to be nearly so critical as in the case of the prior art type applicator device referenced above, thereby substantially simplifying the manufacturing procedure and substantially eliminating the problem of splitting the end of the delivery tip if two or three bristles too many are included in the brush, as well as substantially solving the problem of not holding the brush securely enough if two or three bristles too few are included in the brush.

Furthermore, because the dental agent or coating flows through the spiral, tapered passageway 46 around the bristles 40 rather than through the bristles 40, filler particles are not filtered out by the bristles 40 as in the case of the prior art type device and tip 14 is thus not clogged. Thus, substantially enhanced delivery of the dental agent or coating is accomplished by the delivery tip 14 of the present invention. For example, delivery of semiviscous or viscous material, which may or may not be viscous due to filler, may be virtually impossible to express using the prior art type delivery tip, but yet is easily expressed through the spiral passageway of the delivery tip of this invention.

Figure 6:
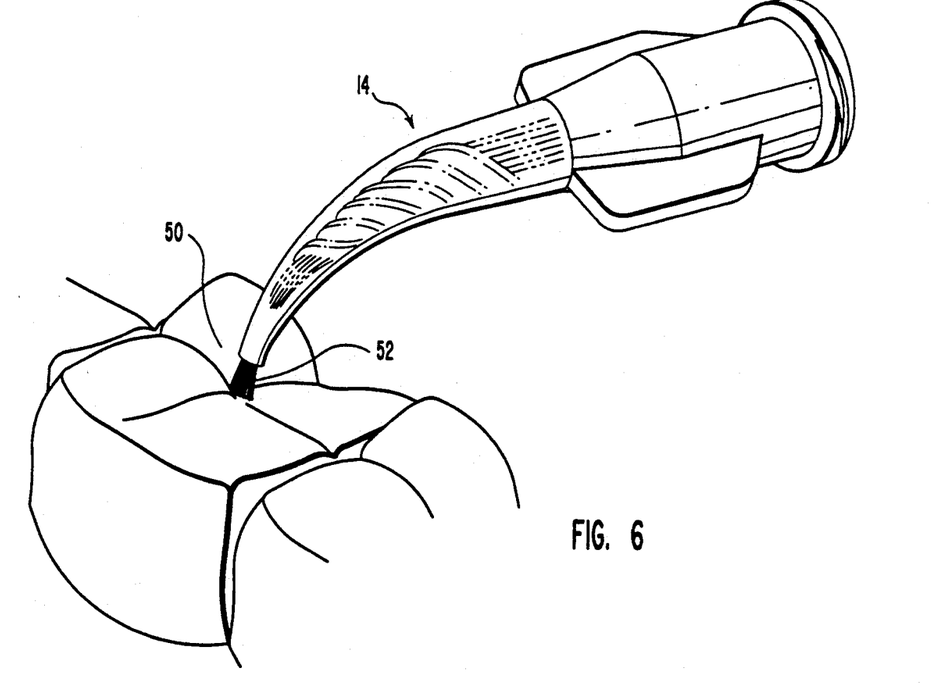
FIG. 6 is an enlarged perspective view which schematically illustrates one presently preferred mode of applying a dental agent or coating to a surface such as a tooth using a pin-point type delivery.
Figure 7:
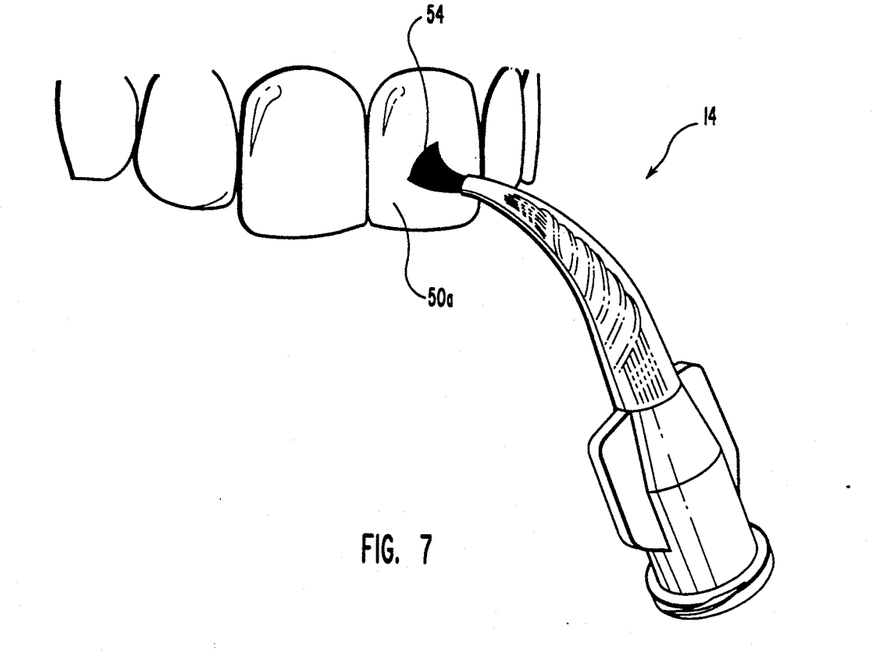
FIG. 7 is an enlarged perspective view which schematically illustrates a fanned out broad-brush type delivery of a dental agent or coating after the bristles have been extended in relation to the distal end of the syringe delivery tip.

In one currently preferred embodiment within the scope of the present invention, the bristle diameter is in the range from about 0.002 inches to about 0.005 inches, and preferably in the range from about 0.0025 inches to about 0.0035 inches. The bristles 40 typically extend beyond the distal end 36 of the delivery tip 14 a distance in the range from about 1/16 inch to about 5/16th inch. The bristles 40 typically extend into the passageway 42 of the delivery tip 14 a distance sufficient to fully engage the helical ridge 44 so that the helical ridge 44 will frictionally hold the bristles 40 but yet will permit the bristles 40 to be pulled out and lengthened if the user of the device so desires in order to permit either a pinpoint type application or a fanned out, broad-brush type application, as described further below in reference to FIGS. 6 and 7. In one preferred embodiment with the scope of the present invention, the bristles extend into the passageway 42 of the delivery tip 14 in a range from about ¼ inch to about ½ inch.

The distance bristles 40 extend beyond the distal end 36 of delivery tip 14 may be manually adjusted by either pushing the bristles 40 further in or pulling them further out. Adjusting the length of the bristles 40 gives even greater control in applying the dental agent or coating. By pushing the bristles 40 further into delivery tip 14, the bristles are stiffer, which allows the dental agent to be worked more easily into surface irregularities such as pits and fissures, using more of a pin-point type control in applying the dental agent or coating. This is shown in conjunction with a tooth surface 50, using a pin-point type length 52 in FIG. 6. By pulling the bristles 40 further out from the delivery tip 14, the user can cause the bristles 40 to fan out and more easily coat a broader surface. This is shown in conjunction with a tooth surface 50a, using a longer length 54 in FIG. 7.

The syringe barrel 12, plunger 22, coupling 18, and delivery tip 14 are preferably constructed of rigid plastic, though other suitable construction materials such as glass or metal may be used. It is also important that the syringe barrel, plunger, coupling, and delivery tip be constructed of a material which will not react with the dental agent or coating used in the syringe. In addition, the dental agent or coating should not adhere to the construction material.

Because many dental agents or coatings are often light sensitive, the applicator 10 may be constructed of a light-resistive material Thus, in that case the syringe barrel 12, delivery tip 14, plunger 20, and coupling 18 are preferably constructed of colored plastic that tends to filter out light. Different colored plastic may be used to identify the type of dental agent or coating within the syringe barrel. Alternatively, printing or other identifying markings on the syringe barrel may be used to identify the type of dental agent or coating. In addition, markings on the outer surface of the syringe barrel or plunger may be used to identify the volume of dental agent or coating used or remaining.

The plunger within the syringe barrel permits controlled dispensing of the dental agent or coating to the surface. It will be appreciated that other means may be used to control dispensing. For example, the applicator may be adapted for capsule use or for squeeze-bulb use.

Although the above discussion has described an apparatus typically used for applying dental agents to tooth surfaces, it will be appreciated that the apparatus may be adapted for applying other coatings to various surface types.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus for controlled delivery of a dental agent to a tooth surface, comprising:
   reservoir means for holding a quantity of dental agent;
   tip means for delivering the dental agent to a desired location on the tooth surface, a proximal end of the tip means being in communication with the reservoir means, said tip means comprising means providing a first passageway from the proximal end of the tip means to a distal end of the tip means;
   brush means secured within the tip means and comprising a first portion which extends sufficiently beyond the distal end of the tip means in order to provide for delivery of the dental agent to the tooth surface and a second portion situated within the first passageway;
   means situated within at least a portion of said first passageway and providing a secondary passageway that is continuously open and unobstructed throughout substantially the entire length of the second portion of the brush means, for delivery of the dental agent around but not through the second portion of the brush means as the dental agent is delivery through said tip means to the first portion of the brush means; and
   means for controlling dispensing of the dental agent from the reservoir means to the distal end of the tip means in order to control the flow of the dental agent onto the tooth surface.

2. An apparatus as defined in claim 1, wherein the tip means is removably attached to the reservoir means.

3. An apparatus as defined in claim 1, wherein the reservoir means comprises a syringe barrel and the controlled dispensing means comprises a plunger located within the syringe barrel for controlling the flow of the dental agent.

4. An apparatus as defined in claim 1, wherein the brush means comprises a plurality of bristles, said bristles extending a distance from the distal end of the tip means in the range from about 1/16 inch to about 5/16 inch.

5. An apparatus as defined in claim 1, wherein the brush means comprises a plurality of bristles, the distance said bristles extend from the distal end of the tip means being adjustable.

6. An apparatus as defined in claims 4 or 5, wherein the bristles are constructed of soft nylon having a diameter in the range from about 0.002 inches to about 0.005 inches.

7. An apparatus as defined in claim 1, wherein said first passageway is tapered from the proximal end of the tip means to the distal end of the tip means.

8. An apparatus as defined in claim 7, wherein said means providing said secondary passageway comprises a helical ridge.

9. An apparatus as defined in claim 8, wherein said brush means is slidably secured by said helical ridge such that the length of said brush means extending beyond the distal end of the tip means is adjustable to provide either a pin-point type application to the tooth surface, or a fanned out, broad-brush type application to the tooth surface.

10. An apparatus for controlling delivery of a dental agent to a tooth surface comprising:
   a reservoir for holding a quantity of dental agent; a generally tubular member for delivering the dental agent to a tooth surface, a proximal end of said tubular member being removably secured to and in communication with the reservoir such that the dental agent flows through the tubular member from the proximal end of the tubular member to a distal end of the tubular member, said tubular member being curved to facilitate application of the dental agent to the tooth surface and said tubular member comprising a means providing a tapered spiral passageway through at least a portion of the tubular member;
   brush means slidably secured within the spiral passageway of the tubular member so as to substantially fill but not occlude the distal end of the tubular member and so as to contact said dental agent within said distal end of the tubular member, said brush means thereby permitting flow of the dental agent around said brush means, and the length of said brush means extending beyond the distal end of the tubular member being slidably adjustable in order to provide for application of the dental agent to the tooth surface using either a pin-point type application to the tooth surface or a fanned out, broad-brush type application to the tooth surface as desired; and
   means for controlling dispensing of the dental agent, said dispensing means being capable of controlling the flow rate of the dental agent from the reservoir onto the tooth surface.

11. An apparatus for applying a dental agent to a tooth surface as defined in claim 10, wherein the tubular member is threadably attached to the reservoir.

12. An apparatus as defined in claim 11, wherein the tubular member is threadably attached to the reservoir.

13. An apparatus as defined in claim 12, wherein the reservoir comprises a syringe barrel and wherein the controlled dispensing means comprises a plunger located within the syringe barrel for controlling the flow of the dental agent.

14. An apparatus as defined in claim 13, wherein the brush means comprises a plurality of bristles secured within the distal end of the tubular member, said bristles extending a distance from the distal end of the tubular member in the range from about 1/16 inch to about 5/16 inch.

15. An apparatus as defined in claim 14, wherein the bristles are constructed of soft nylon having a diameter in the range from about 0.002 inches to about 0.005 inches.

16. An apparatus as defined in claim 11, wherein the tubular member is attached to the reservoir with a luer-lock.

17. An apparatus as defined in claim 11, wherein the tubular member is permanently secured to the reservoir.

18. An apparatus for controlling delivery of a dental agent to a tooth surface comprising:
   a reservoir for holding a quantity of dental agent, said reservoir being constructed of a chemically insert material with respect to the dental agent;
   a generally tubular member for applying the dental agent to a tooth surface, a proximal end of said tubular member being in communication with the reservoir such that the dental agent flows through the tubular member from the proximal end of the tubular member to a distal end of the tubular member, said tubular member being curved to facilitate application of the dental agent to the tooth surface and said tubular member comprising a means providing a tapered spiral passageway through at least a portion of the tubular member;
   a brush, comprising a plurality of bristles slidably secured within but not totally occluding the spiral passageway of the tubular member, said brush being dimensioned so as to substantially fill but not occlude the distal end of the tubular member, said brush thereby permitting flow of the dental agent around the bristles and through the spiral passageway and out of the distal end of the tubular member, at least a portion of said brush extending sufficiently beyond the distal end of the tubular member in order to provide for application of the dental agent to the tooth surface and wherein the length of the brush extending beyond the distal end of the tubular member is slidably adjustable in order to provide for application of the dental agent to the tooth surface using either a pin-point type application to the tooth surface or a fanned out, broad-brush type application to the tooth surface as desired; and
   means for controlling dispensing of the dental agent, said dispensing means being capable of controlling the flow rate of the dental agent from the reservoir onto the predetermined tooth surface.

19. An apparatus as defined in claim 18, wherein said means providing said spiral passageway comprises a helical ridge.

20. An apparatus as defined in claim 19, wherein said brush means is slidably secured by said helical ridge such that the length of said brush means extending beyond the distal end of the tip means is adjustable to provide either a pin-point type application to the tooth surface, or a fanned out, broad-brush type application to the tooth surface.

21. An apparatus as defined in claim 20, wherein the helical ridge is dimensioned to provide friction between the bristles and the helical ridge secures the bristles in place.

22. An apparatus as defined in claim 21, wherein the bristles are constructed of soft nylon having a diameter in the range from about 0.002 inches to about 0.005 inches.

23. An apparatus as defined in claim 22, wherein the tubular member is removably attached to the reservoir.

24. An apparatus as defined in claim 23, wherein the tubular member is attached to the reservoir with a luer-lock coupling.

25. An applicator tip for delivering dental agent from a syringe barrel to a tooth surface, comprising:
a generally tubular member for delivering dental agent to a tooth surface, a proximal end of said tubular member being configured to be removably attached to the syringe barrel, said tubular member being curved to facilitate precise application of the dental agent to the tooth surface, and said tubular member comprising a means providing a tapered spiral passageway through at least a portion of the tubular member; and
a brush, comprising a plurality of bristles slidably secured within the spiral passageway of the tubular member, said brush being dimensioned to permit flow of the dental agent through said spiral passageway and around said bristles, and the length of said brush extending beyond the distal end of the tubular member being slidably adjustable in order to provide for application of the dental agent to the tooth surface using either a pin-point type application to the tooth surface or a fanned out, broad-brush type application of dental agent to the tooth surface as desired.

26. An apparatus for controlled delivery of a dental bonding agent to a tooth surface, comprising:
a hollow barrel comprising a reservoir for holding a quantity of dental bonding agent, said barrel being constructed of a chemically inert material with respect to the dental bonding agent, and said reservoir being sufficiently opaque to prevent light-initiated activation of the bonding agent;
a generally tubular member for delivering dental bonding agent to a tooth surface, a proximal end of said tubular member being removably secured to and in communication with the reservoir such that the dental bonding agent flows through the tubular member from the proximal end of the tubular member to a distal end of the tubular member, said tubular member being curved to facilitate precise application of the bonding agent to the predetermined tooth surface, and said tubular member comprising a means providing a tapered spiral passageway through at least a portion of the tubular member;
a brush, comprising a plurality of bristles slidably secured within but not occluding the spiral passageway of the tubular member, said brush permitting flow of the dental bonding agent through the spiral passageway and around said bristles, at least a portion of said brush extending sufficiently beyond the distal end of the tubular member in order to provide for application of the dental bonding agent to the tooth surface and wherein the length of the brush extending beyond the distal end of the tubular member is slidably adjustable in order to provide for application of the dental bonding agent to the tooth surface using either a pin-point type application to the tooth surface or a fanned out, broad-brush type application to the tooth surface as desired; and
a plunger having a plunger head longitudinally moveable within the barrel, said plunger controlling the flow rate of the bonding agent from the barrel and onto the tooth surface.

27. An apparatus as defined in claim 26, wherein said means providing said spiral passageway comprises a helical ridge.

28. An apparatus as defined in claim 27, wherein said brush is slidably secured by said helical ridge such that the length of said brush extending beyond the distal end of the tip means is adjustable to provide either a pin-point type application to the tooth surface, or a fanned out, broad-brush type application to the tooth surface.

29. An apparatus as defined in claim 28, wherein the helical ridge is dimensioned to provide friction between the bristles and the tubular member secures the bristles in place.

30. An apparatus as defined in claim 29, wherein the bristles are constructed of soft nylon having a diameter in the range from about 0.002 inches to about 0.005 inches.

31. An apparatus for controlled delivery of a coating material to a surface, comprising:
reservoir means for holding a quantity of the coating material;
tip means for delivering the coating material to a desired location on the surface, a proximal end of the tip means being in communication with the reservoir means, said tip means comprising means providing a first passageway from the proximal end of the tip means to a distal end of the tip means;
brush means secured within the tip means and comprising a first portion which extends sufficiently beyond the distal end of the tip means in order to provide for delivery of the coating material to the surface and a second portion situated within the first passageway;
means situated within at least a portion of said first passageway and providing a secondary passageway that is continuously open and unobstructed throughout substantially the entire length of the second portion of the brush means, for delivery of the coating material around but not through the second portion of the brush means as the coating material is delivered through said tip means to the first portion of the brush means; and
means for controlled dispensing of the coating material from the reservoir means to the distal end of the tip means in order to control the flow of the coating material onto the surface.

32. An apparatus defined in claim 31, wherein said first passageway is tapered from the proximal end of the tip means to the distal end of the tip means.

33. An apparatus as defined in claim 32, wherein said means providing said secondary passageway comprises a helical ridge.

34. An apparatus as defined in claim 33, wherein said brush means is slidably secured by said helical ridge such that the length of said brush means extending beyond the distal end of the tip means is adjustable to provide either a pin-point type application to the surface, or a fanned out, broad-brush type application to the surface.

* * * * *

UNITED STATES PATENT AND TRADEMARK OFFICE
CERTIFICATE OF CORRECTION

PATENT NO.   : 5,269,684
DATED        : December 14, 1993
INVENTOR(S)  : DAN E. FISCHER It is certified that error appears in the above-indentified patent and that said Letters Patent is hereby corrected as shown below:

```
Column 5, line 10, after "14" insert --.--
Column 5, line 53, "FIGS. 14" should be --FIGS. 1-4--
Column 5, line 65, after "application" insert --.--
Column 8, line 6, after "material" insert --.--
Column 10, line 3, "t he" should be --the--
Column 10, line 26, "insert" should be --inert--
```

Signed and Sealed this

Sixteenth Day of August, 1994

Attest:

BRUCE LEHMAN

*Attesting Officer*     *Commissioner of Patents and Trademarks*